US009650316B2

(12) United States Patent
Caciula et al.

(10) Patent No.: US 9,650,316 B2
(45) Date of Patent: May 16, 2017

(54) LOW EMISSIONS OXIDATIVE DEHYDROGENATION PROCESS FOR PRODUCING BUTADIENE

(71) Applicant: TPC Group LLC, Houston, TX (US)

(72) Inventors: Liana Caciula, Houston, TX (US);
Joseph G. Duff, League City, TX (US);
Elizabeth Ballard, Houston, TX (US);
Sirisha Chada, Houston, TX (US);
Mark J. Potter, Houston, TX (US)

(73) Assignee: TPC GROUP LLC, Houston, TX (US)

( * ) Notice: Subject to any disclaimer, the term of this patent is extended or adjusted under 35 U.S.C. 154(b) by 159 days.

(21) Appl. No.: 14/386,617

(22) PCT Filed: Mar. 28, 2013

(86) PCT No.: PCT/US2013/034205
§ 371 (c)(1),
(2) Date: Sep. 19, 2014

(87) PCT Pub. No.: WO2013/148908
PCT Pub. Date: Oct. 3, 2013

(65) Prior Publication Data
US 2015/0080627 A1 Mar. 19, 2015

Related U.S. Application Data

(60) Provisional application No. 61/617,506, filed on Mar. 29, 2012, provisional application No. 61/617,535, filed on Mar. 29, 2012.

(51) Int. Cl.
*C07C 5/48* (2006.01)
*B01J 19/24* (2006.01)
(Continued)

(52) U.S. Cl.
CPC .............. *C07C 5/48* (2013.01); *B01J 19/24* (2013.01); *C07C 5/09* (2013.01); *C07C 7/005* (2013.01);
(Continued)

(58) Field of Classification Search
CPC .. C07C 5/48; C07C 7/005; C07C 5/09; C07C 2527/185; C07C 2523/80; C07C 2523/745; C07C 5/321; C07C 11/167
(Continued)

(56) References Cited

U.S. PATENT DOCUMENTS 3,159,588 A   12/1964 Hansford
3,207,805 A    9/1965 Guy
(Continued)

FOREIGN PATENT DOCUMENTS

SU    1216938 A1    10/1999

OTHER PUBLICATIONS

"Reduce Natural Gas Use in Your Industrial Process Heating Systems" (Sep. 2007), U.S. Department of Energy: Energy Efficiency and Renewable Energy, pp. 1-2.*
(Continued)

*Primary Examiner* — In Suk Bullock
*Assistant Examiner* — Aaron Pierpont
(74) *Attorney, Agent, or Firm* — Michael W. Ferrell

(57) ABSTRACT

Butadiene is formed by dehydrogenation of butenes which are mixed with steam and oxygen then converted to butadiene by oxidative dehydrogenation over a ferritic oxide catalyst, wherein the sensible heat in the oxidative dehydrogenation reaction product is utilized along with heat produced by thermal oxidation of low value volatile products formed to reduce energy requirements and $CO_2$ emissions. Sensible heat is utilized at high temperature for purposes of
(Continued)

superheating feed and at somewhat lower temperatures for purposes of vaporizing feed at sequential locations in the process.

15 Claims, 6 Drawing Sheets

(51) Int. Cl.
    *C07C 7/00*         (2006.01)
    *C07C 5/09*         (2006.01)
    *B01J 23/889*      (2006.01)
    *B01J 27/187*      (2006.01)

(52) U.S. Cl.
    CPC .......... *B01J 23/8892* (2013.01); *B01J 27/187* (2013.01); *B01J 2219/24* (2013.01); *B01J 2523/00* (2013.01); *C07C 2523/745* (2013.01); *C07C 2523/80* (2013.01); *C07C 2527/185* (2013.01)

(58) Field of Classification Search
    USPC ................................ 585/315, 602, 601, 616
    See application file for complete search history.

(56) References Cited

U.S. PATENT DOCUMENTS

| | | | |
|---|---|---|---|
| 3,284,536 A | | 11/1966 | Bajars et al. |
| 3,320,330 A | | 5/1967 | Callahan et al. |
| 3,322,847 A | * | 5/1967 | Szabo .................... C07C 5/48 585/622 |
| 3,496,070 A | | 2/1970 | Woerner et al. |
| 3,674,887 A | * | 7/1972 | Clay ...................... C07C 5/48 585/621 |
| 3,745,194 A | | 7/1973 | Bertus et al. |
| 3,801,670 A | | 4/1974 | Shiraishi et al. |
| 3,801,671 A | | 4/1974 | Marscheck |
| 3,900,525 A | | 8/1975 | Christmann et al. |
| 3,937,746 A | | 2/1976 | Croce et al. |
| 3,943,185 A | | 3/1976 | Tschopp |
| 3,953,370 A | | 4/1976 | Miklas |
| 4,067,921 A | | 1/1978 | Helberg |
| 4,083,884 A | * | 4/1978 | Purdy .................... C07C 5/48 502/329 |
| 4,479,025 A | * | 10/1984 | Imai ..................... C07C 15/46 208/134 |
| 4,658,074 A | | 4/1987 | Bajars et al. |
| 4,740,334 A | | 4/1988 | Rukovena, Jr. |
| 4,973,793 A | | 11/1990 | McFarland |
| 4,975,407 A | | 12/1990 | Dejaifve et al. |
| 5,139,988 A | | 8/1992 | Sasaki et al. |
| 5,772,898 A | | 6/1998 | Lewis |
| 6,874,769 B2 | | 4/2005 | Lantz et al. |
| 2007/0179330 A1 | | 8/2007 | Johann et al. |
| 2010/0261938 A1 | * | 10/2010 | Olah .................... C07C 29/151 568/840 |
| 2011/0245568 A1 | | 10/2011 | Khabashesku et al. |

OTHER PUBLICATIONS

European Search Report dated Nov. 10, 2015.
Welch, et al., "Butadiene Via Oxidative Dehydrogenation", Hydrocarbon Processing, Nov. 1978, pp. 131-136.
Japanese Office Action and Search Report dated Sep. 28, 2015.
Russian Search Report, with translation, dated Mar. 6, 2017.

* cited by examiner

LOW EMISSIONS OXIDATIVE DEHYDROGENATION PROCESS FOR PRODUCING BUTADIENE

CROSS-REFERENCE TO RELATED APPLICATION(S)

This National Phase Application is based on International Application No. PCT/US2013/034205 of the same title filed Mar. 28, 2013, the priority of which is hereby claimed and the disclosure of which is incorporated herein by reference.

The International Patent Application was based on U.S. Provisional Patent Application Ser. No. 61/617,506 of the same title, filed Mar. 29, 2012, the priority of which is hereby claimed and the disclosure of which is incorporated herein by reference in its entirety.

The International Patent Application was also based on U.S. Provisional Patent Application Ser. No. 61/617,535, entitled, "IMPROVED CONTROLLABILITY OXIDATIVE DEHYDROGENATION PROCESS FOR PRODUCING BUTADIENE", filed Mar. 29, 2012, the priority of which is hereby claimed and the disclosure of which is incorporated herein by reference in its entirety.

TECHNICAL FIELD

The present invention relates to oxidative dehydrogenation of butenes to make butadienes. The butadiene enriched product stream is used to provide heat for the reaction section by staged indirect heat exchange. Thermal oxidation of organic compounds separated from the butadiene enriched product stream also provides energy to the reaction section.

BACKGROUND OF THE INVENTION

Previously known oxidative dehydrogenation processes for producing butadiene from hydrocarbons have used natural gas fired heaters to vaporize and superheat the reaction feed streams and consequently have produced emissions, particularly $CO_2$ emissions, far in excess of the level acceptable in today's climate. In particular, previous processes typically used natural gas to vaporize butene and heat a mixture of hydrocarbons, preferably butenes, oxygen and steam to a temperature in excess of 260° C. (500° F.), more commonly in excess of about 315° C. (600° F.), and preferably over about 345° C. (650° F.) or, in some cases, even over 371° C. (700° F.). In a typical process, the reaction mixture includes butenes, oxygen in an amount of from about 0.4 moles to about 0.8 moles, more typically from slightly in excess of 0.5 moles up to about 0.65 moles of oxygen for each mole of butene in the butene rich hydrocarbonaceous feed, and superheated steam in amounts of from about 12:1 to about 16:1. Subsequent to reaction, the reaction product mixture is cooled and butadiene separated by oil absorption and subsequent fractionation. Typically, these processes produce crude butadiene at a purity ranging from about 50 to about 70%, more typically from about 55 to about 65%, which is passed onward in the plant for further processing using known technologies.

References of interest are discussed below.

Lewis; HYDROCARBON CONVERSION PROCESS USING NOVEL METALLO MANGANESE OXIDES; U.S. Pat. No. 5,772,898; Jun. 30, 1998; relates to a hydrocarbon conversion process comprising contacting a hydrocarbon feed with a catalyst comprising a crystalline metallo manganese oxide composition having a three-dimensional framework structure, an intracrystalline pore system and an empirical chemical composition on an anhydrous basis expressed by the formula:

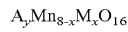

where A is a templating agent selected from alkali metals, alkaline earth metals and ammonium ion, "y" is the moles of A and varies from the group consisting of about 0.5 to about 2.0, M is a metal selected from the group consisting of chromium, zirconium, tin, platinum, rhodium, niobium, tantalum, vanadium, antimony, ruthenium, gallium and germanium, "x" is the moles of M and varies from about 0.01 to about 4.0 and characterized in that manganese has a valence of +3, or +4, M has a valence of +3, +4 or +5 and the composition has the hollandite structure.

Sasaki et al.; IRON-ANTIMONY-CONTAINING METAL OXIDE CATALYST COMPOSITION AND PROCESS FOR PRODUCING THE SAME; U.S. Pat. No. 5,139,988; Aug. 18, 1992; relates to a composition which contains as essential components: crystalline iron antimonate and at least one element selected from the group consisting of vanadium, molybdenum, and tungsten; is useful as a catalyst in the oxidation reaction of organic compounds. Also, a process for producing the composition is disclosed.

Dejaifve et al.; CATALYST FOR DEHYDROGENATING ORGANIC COMPOUNDS, A PROCESS FOR ITS PREPARATION AND ITS USE; U.S. Pat. No. 4,975,407; Dec. 4, 1990; relates to a catalyst derived from iron oxides providing agents and potassium oxide providing agents, characterized in that the molar ratio is in the range of from 1.5 to 60 and that a potassium ferrite $K_2Fe_{12}O_{19}$ phase is present supported on an octahedral $Fe_3O_4$ matrix, showing crystalline epitaxy between the hexagonal structure of $K_2Fe_{12}O_{19}$ and the (111) planes of the $Fe_3O_4$ spinel structure.

McFarland; OXIDATIVE DEHYDROGENATION OF AMYLENES; U.S. Pat. No. 4,973,793; Nov. 27, 1990; relates to an oxidative dehydrogenation process wherein butylenes are cofed with amylenes in a catalytic oxidative dehydrogenation reaction which is said to substantially improve the conversion of the amylenes. The improved amylene conversion is obtained by the oxidative dehydrogenation of mixtures of amylenes and from 10 to 95 mole % butylenes.

Heiberg, U.S. Pat. No. 4,067,921, discloses heat recovery in connection with a butadiene production operation. See FIG. 4 and the text at Col. 6, lines 20-38.

Miklas, METHOD OF ACTIVATING ZINC-FERRITE OXIDATIVE DEHYDROGENATION CATALYST; U.S. Pat. No. 3,953,370; Apr. 27, 1976, relates to use of steam at a temperature of from 370-700° C. (700-1300° F.) to activate a zinc ferrite oxidative dehydrogenation catalyst for preparation of butadiene from $C_4$-$C_8$ hydrocarbons.

Tschopp; DIOLEFIN PRODUCTION AND PURIFICATION; U.S. Pat. No. 3,943,185; Mar. 9, 1976 relates to a process for producing a stream of oxidatively dehydrogenated $C_4$ hydrocarbons substantially free of oxygen and inert noncondensable gases removed comprising absorbing the $C_4$ hydrocarbons in an absorber oil in a first zone; stripping oxygen and inert noncondensable gases from the mixture of adsorber oil and $C_4$ hydrocarbons in a second zone which is operated under conditions of temperature and pressure to maintain an aqueous phase in the second zone; and withdrawing (1) a predominately aqueous phase from the second zone, (2) an overhead of predominately all of the oxygen and inert noncondensable gases and a bottoms of adsorber oil and C4 hydrocarbon substantially free of oxygen and inert noncondensable gases.

In Croce et al.; SULFUR PROMOTED OXIDATIVE DEHYDROGENATION; U.S. Pat. No. 3,937,746; Feb. 10, 1976; the yield in oxidative dehydrogenation of organic compounds is improved by having a sulfur promoter present either as part of the catalyst or added to the reaction with the reactants.

In Marsheck; OXIDATIVE DEHYDROGENATION OF ORGANIC COMPOUNDS; U.S. Pat. No. 3,801,671; Apr. 2, 1974; it is reported that the oxidative dehydrogenation of paraffinic hydrocarbons to diolefins can be improved by effecting such dehydrogenation in the presence of a fluidized mixed catalyst system consisting essentially of at least one catalyst active for the conversion of paraffins in admixture with at least one catalyst active for the conversion of monoolefins.

In Bertus, et al.; OXIDATIVE DEHYDROGENATION OF PARAFFINIC HYDROCARBONS; U.S. Pat. No. 3,745,194; Jul. 10, 1973; organic compounds are dehydrogenated to compounds having a higher degree of unsaturation by contacting the feedstock in the vapor phase in the presence of an oxygen containing gas with a catalyst containing tin in an oxidized state in combination with at least one of the metals bismuth, cobalt, or nickel in an oxidized state. Representative of such conversions is the oxidative dehydrogenation of butane to 1,3-butadiene over a nickel stannate-containing catalyst.

In Woerner et al; PURIFICATION OF UNSATURATED HYDROCARBONS BY EXTRACTIVE DISTILLATION WITH ADDITION OF LIQUID SOLVENT TO STRIPPER OVERHEAD; U.S. Pat. No. 3,496,070; Feb. 17, 1970, a hydrocarbon separation process is provided for the separation of a hydrocarbon mixture comprising 4 to 5 carbon atoms including unsaturated hydrocarbons which comprises: extractively distilling the hydrocarbon mixture with a selective solvent in an extractive distillation column whereby hydrocarbon is selectively extracted in the extractive distillation column to form a hydrocarbon-rich solvent fraction which is fed to a solvent stripping column with said solvent being taken off as a bottoms from said stripping column and a vaporous hydrocarbon fraction being taken as an overhead fraction from said stripping column; adding said selective solvent in liquid phase to the vaporous overhead from the solvent stripper to lower the pressure in the overhead condenser of the solvent stripper column and in the solvent stripper.

Bajars; DEHYDROGENATION WITH MAGNESIUM FERRITE; U.S. Pat. No. 3,284,536; Nov. 8, 1966 relates to dehydrogenating hydrocarbons in the vapor phase at elevated temperatures in the presence of oxygen and a catalyst containing magnesium ferrite. Hydrocarbons to be dehydrogenated according to the process are hydrocarbons of 4 to 7 carbon atoms, preferably aliphatic hydrocarbons selected from the group consisting of saturated hydrocarbons, monoolefins, diolefins and mixtures thereof of 4 to 5 or 6 carbon atoms having a straight chain of at least four carbon atoms, and cycloaliphatic hydrocarbons. Oxygen is present in the reaction zone in an amount within the range of 0.2 to 2.5 mols of oxygen per mol of hydrocarbon to be dehydrogenated. The temperature for the dehydrogenation reaction will be greater than 250° C., such as greater than about 300° C. or 375° C., and the maximum temperature in the reactor may be about 650° C. or 750° C. or perhaps higher under certain circumstances.

Gay; DEHYDROGENATION IN THE PRESENCE OF OXYGEN AND AN AMMONIUM HALIDE; U.S. Pat. No. 3,207,805; Sep. 21, 1965 relates to a process for dehydrogenating organic compounds and relates more particularly to the dehydrogenation of dehydrogenatable organic compounds at elevated temperatures in the presence of oxygen and an ammonium halide.

Welch, et al., in "BUTADIENE VIA OXIDATIVE DEHYDROGENATION", Hydrocarbon Processing, November 1978, pp. 131-136; discuss an oxidative dehydrogenation process, in which steam, air or oxygen, and normal butenes are heated and passed over an undisclosed autoregenerative heterogeneous catalyst at around 430° C. (800° F.) using steam as a heat sink to moderate the temperature rise in the adiabatic reactor system without using gas phase additives such as halogen and sulfur compounds. The process is said to consume essentially all of the oxygen in the feed usually leaving oxygen levels in the effluent below 0.3 percent. Acetylenes and oxygenated byproducts are major by products.

SUMMARY OF THE INVENTION

The present invention provides a low emissions method of manufacturing butadiene from a butene rich feed, wherein butenes are mixed with steam and oxygen then converted to butadiene by oxidative dehydrogenation over a ferritic oxide catalyst. Sensible heat in the oxidative dehydrogenation reaction product is utilized along with heat produced by thermal oxidation of low value volatile products formed to reduce energy requirements and $CO_2$ emissions. Sensible heat is utilized at high temperature for purposes of superheating feed and at somewhat lower temperatures for purposes of vaporizing feed.

A typical process includes providing a butene rich hydrocarbonaceous feed, vaporizing and superheating said hydrocarbonaceous butene rich feed to a temperature of at least about 205° C. (400° F.), mixing said hydrocarbonaceous butene rich feed with superheated steam and an oxygen rich gas to form a reactor feed stream, the moles of oxygen in said reactor feed stream being controlled to fall in the range of at least about 0.4, more preferably at least about 0.5 moles of oxygen per mole of hydrocarbonaceous butene rich feed, reacting said reactor feed stream over a ferritic oxide catalyst, preferably an oxide catalyst comprising: a major proportion of iron; a minor proportion of zinc; and smaller amounts of manganese; phosphorus derived from a phosphorus source such as phosphoric acid; and preferably calcium derived from a non-nitrogenous calcium precursor such as calcium acetate; thereby forming a butadiene enriched product stream, wherein: the catalyst bed is preheated to a temperature which is sufficient to initiate the oxidative dehydrogenation reaction by passing an inert or reductive feed stream, often natural gas, but possibly butene if more convenient, and steam in the absence of oxygen, through the catalyst bed until it reaches a temperature of about 345° C. (650° F.) up to a bed temperature of at least about 425° C.-455° C. (800° F.-850° F.), depending on the activity of the catalyst. The steam in the flow used for getting the catalyst bed up to temperature is superheated using natural gas or some other convenient external energy source. Once the catalyst bed has been adequately heated, if the reductive agent is natural gas, it is replaced by butenes. In the case where butene has been used as the reductive agent, air containing the oxygen required for the reaction is introduced, and the superheated steam flow is controlled to maintain the mixed reactor feed temperature at desired level. The reactor effluent used to provide heat required to the feed, usually heating the reactor feed stream to at least about 315° C. to 345° C. (600° F. to 650° F.). The butadiene rich reactor effluent, which is typically at about 595° C. (1100° F.), is used on the hot side of a series of heat exchangers; passing first through a reactor feed superheater in which the combined flow of butenes and steam directed to the reactor is usually superheated to at least about 205° C. (400° F.), usually from about 315° C. to 345° C. (600° F. to 650° F.), by indirect heat exchange with said butadiene enriched product stream. In some cases, the butadiene enriched product stream passes next through a recycle condensate vaporizer in which steam is generated by indirect heat exchange (as mentioned, the steam being subsequently mixed with butenes and the resulting mixture being superheated by said butadiene enriched product stream just prior to entering the reactor); the butadiene enriched product stream, after cooling to a temperature in the range of 175° C. to about 125° C. (350° F. to about 260° F.), preferably about 130° C. to 150° C. (280° F. to 300° F.), being directed through a quench column, in which heat is removed from the butadiene enriched product stream and steam content thereof condensed. It is often preferable to vaporize aqueous condensate with high pressure steam generated by combustion of low value organics removed from the process stream as described below.

After passing through the quench column, the butadiene enriched product stream may be conducted to a suction drum in which any liquids entrained in the product stream are removed prior to passing through a two-stage compressor with inter-stage cooling. Alternatively, the suction drum may be dispensed with if the top of the quench tower is correctly sized for vapor/liquid disengagement and a demister pad is provided to intercept suspended droplets that might otherwise pass from the quench tower to the compressor. After being compressed to about 1140 kPa abs. (150 psig), the butadiene enriched product stream is directed to an aldehyde scrubber, and ultimately, a C4 absorber. After removal of aldehydes in the aldehyde scrubber, the C4 species contained in the butadiene enriched product stream are removed in the C4 absorber column by absorption into a compatible absorption oil, which is adapted to preferentially absorb butadiene and other C4's, leaving nitrogen, hydrogen, and lighter hydrocarbon species to be removed in a gaseous overhead stream which is directed to a thermal oxidizer equipped with heat recovery to supply high pressure steam to be used to supply heat, as mentioned previously particularly heat for vaporizing recovered aqueous condensate used producing the superheated steam needed for the oxidative dehydrogenation reaction. Preferably, off-gases having more value as fuel than as products or reactants removed during other processing steps or in other operations in the plant are also directed to the thermal oxidizer; but a large source of the energy in the feed to the thermal oxidizer derives from the gaseous products not absorbed in the C4 absorber column. In some cases, it will be expedient to augment the feed to the thermal oxidizer with natural gas or some other vaporous feed so that a stable flame is obtained in the thermal oxidizer. In this case, the heat value obtained by combustion of the recovered low value organics can supply a large portion of the heat required for vaporization of the recovered aqueous condensate, the energy required for this vaporization being a large component of the energy needs of the process, although since the BTUs are of course fungible, it may not be possible to directly track them to the vaporizer. A particularly useful source of combustible organics for the thermal oxidizer lies in the downstream processes for purification of crude butadiene into salable product. In cases, where alkanes are dehydrogenated on site to provide the butenes fed to the oxidative dehydrogenation process, the off-gases from that process can be another useful source of energy.

After passing through the C4 absorber column, the absorber oil having butadiene dissolved therein is directed to a degasser tower where carbon dioxide, residual nitrogen and hydrogen are removed overhead and sent back to the second stage of the gas compressor, the absorber oil being passed thence to a C4 stripper wherein dispersed organics dissolved in the absorber oil are stripped out, the absorber oil being cooled and recirculated to the C4 absorber via the lean oil surge drum. Preferably, during steady operation of the plant which normally continues for many months at a time, over 40% of the heat required to vaporize both the hydrocarbonaceous butene rich feed and the condensate recovered from the butadiene enriched product stream is primarily supplied by sensible heat recovered from the butadiene enriched product stream as well as by heat generated by thermal oxidation of undesired products removed from two sources: (1) the butadiene enriched product stream, and (2) undesired products created during production of butenes from alkanes, such that at least 40%, preferably at least about 45%, of the energy required for manufacturing butadiene is supplied by the energy content of the feed stocks for the operation as the vast majority of the energy required is used for vaporizing and superheating the feeds to the reactor. For example in a plant having a capacity of about 32,000 kg of butadiene per hour (70 thousand lbs of butadiene per hour), approximately 21,000 kJ are required for each kg (9000 BTUs are required for each lb) of butadiene produced; so at least about 3800 kJ to about 4200 kJ (about 3600 BTUs to about 4000 BTUs) can be supplied by recovery of sensible heat from the reactor effluent. In this regard, it is considered significant that much of the energy recovered comes from a high to medium quality heat source at about 595° C. (1100° F.) and is only required to pass through one tube wall in the recovery process. Further, by separating combustible organics from the condensate, the water content of the butadiene enriched product stream is cleaned so that it can be vaporized to generate steam and reused as required for the oxidative dehydrogenation reactors, so that, as compared to prior art processes, the net energy and water usage of the process of the present invention can be very low. In cases, where a thermal oxidizer is used, an additional 10 to 40% of the energy required, about 2100 to about 8400 kJ/kg (about 900 to about 3600 BTUs per lb) of butadiene, depending on the size of the thermal oxidizer, can be supplied by combustion of combustible organics.

In one embodiment of the present invention, the heat required to vaporize both the hydrocarbonaceous butene rich feed and the water stripped from the butadiene enriched product stream is augmented by available heat generated by associated plant equipment such that in steady operation, the energy required for manufacturing crude butadiene from a butene rich feed is supplied by the energy content of the feed to the combined dehydrogenation and oxidative dehydrogenation process as well as available heat generated by associated plant equipment with less than about 12,800 kJ/kg (about 5500 BTUs per lb) of butadiene, preferably less than about 11,500 kJ/kg (about 5000 BTUs per lb) of butadiene, being supplied by fossil fuels. In cases where a thermal oxidizer is employed, the energy required from fossil fuels can be less than about 10,500 kJ/kg (about 4500 BTU per pound) of butadiene down to less than 5800 kJ/kg (2500 BTUs per pound) of butadiene.

BRIEF DESCRIPTION OF THE DRAWINGS

The invention is described in detail below with reference to numerous examples and the appended Figures wherein like numbers designate similar parts throughout and wherein.

DETAILED DESCRIPTION

The invention is described in detail below in connection with the Figures for purposes of illustration, only. The invention is defined in the appended claims. Terminology used throughout the specification and claims herein are given their ordinary meanings, for example, "indirect heat transfer" refers to heat transfer from one medium to another medium through a heat exchanger wall and pressures refer to gauge pressures unless otherwise indicated. When carrying out the inventive process, preferably heat is transferred through a single heat exchanger wall from a higher temperature stream to a lower temperature stream, such as from reactor effluent to reactor feed in a feed superheater as described hereinafter. Indirect heat transfer may be carried out in accordance with the invention using any suitable equipment such as tube and shell heat exchangers or plate and frame heat exchangers.

Unless otherwise indicated, "butadiene" or "BD" refers to 1,3 butadiene or mixtures comprising 1,3 butadiene.

"Temperature delta" refers to a temperature difference, for example, the temperature difference between the input temperature of a stream provided to a heat exchange device and the output (exit) temperature of that stream from that heat exchange device. A temperature delta of a stream though a heat exchanger is thus the difference between the inlet temperature and outlet temperature of that stream.

The front end of butadiene production system of the present invention comprises multiple largely identical process trains, each process train having one reactor 30 producing a butadiene enriched product stream from which useful heat is extracted by indirect heat exchange before entering quench tower 64 at which point all process streams are combined in our preferred embodiment. Only one train will be illustrated to avoid needless over-complication.

Figure 1:
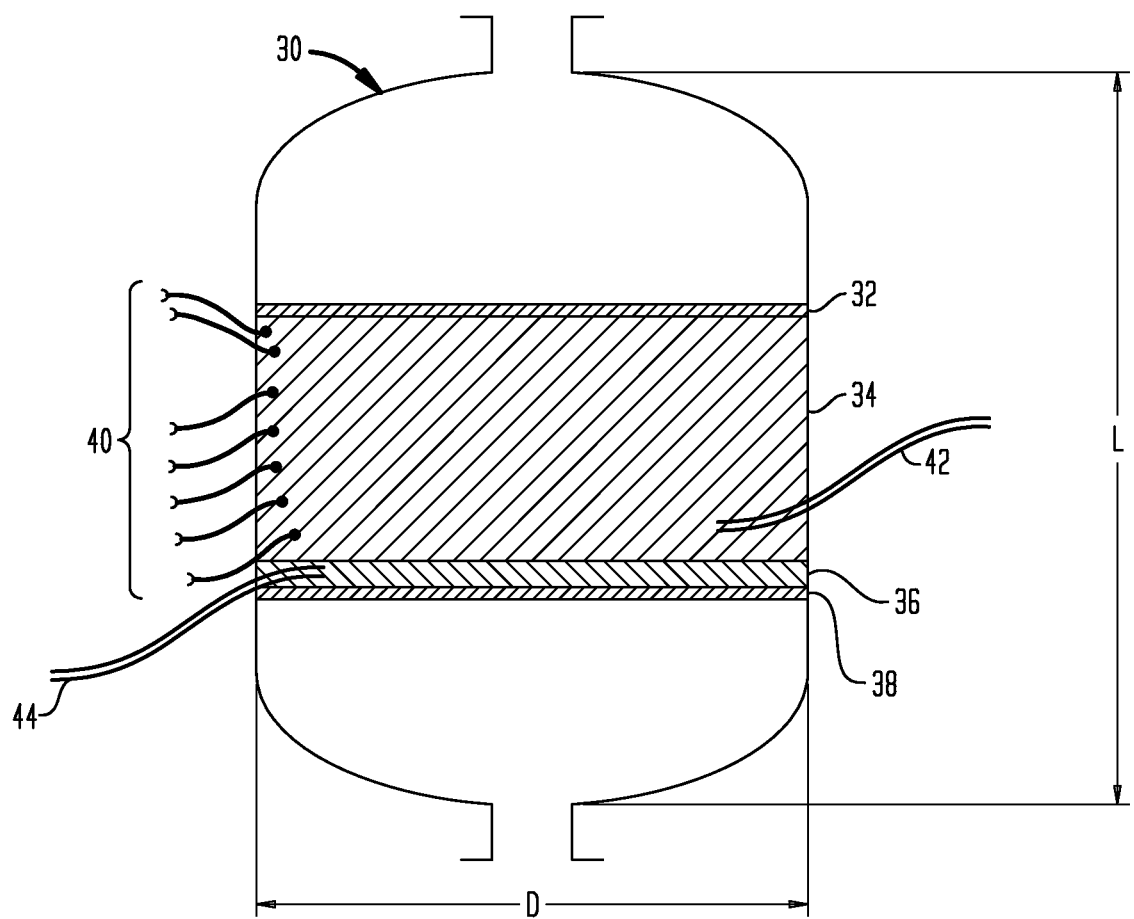
FIG. 1 is a schematic sectional view of a preferred reactor for use in the practice of the present invention.
Figure 2:
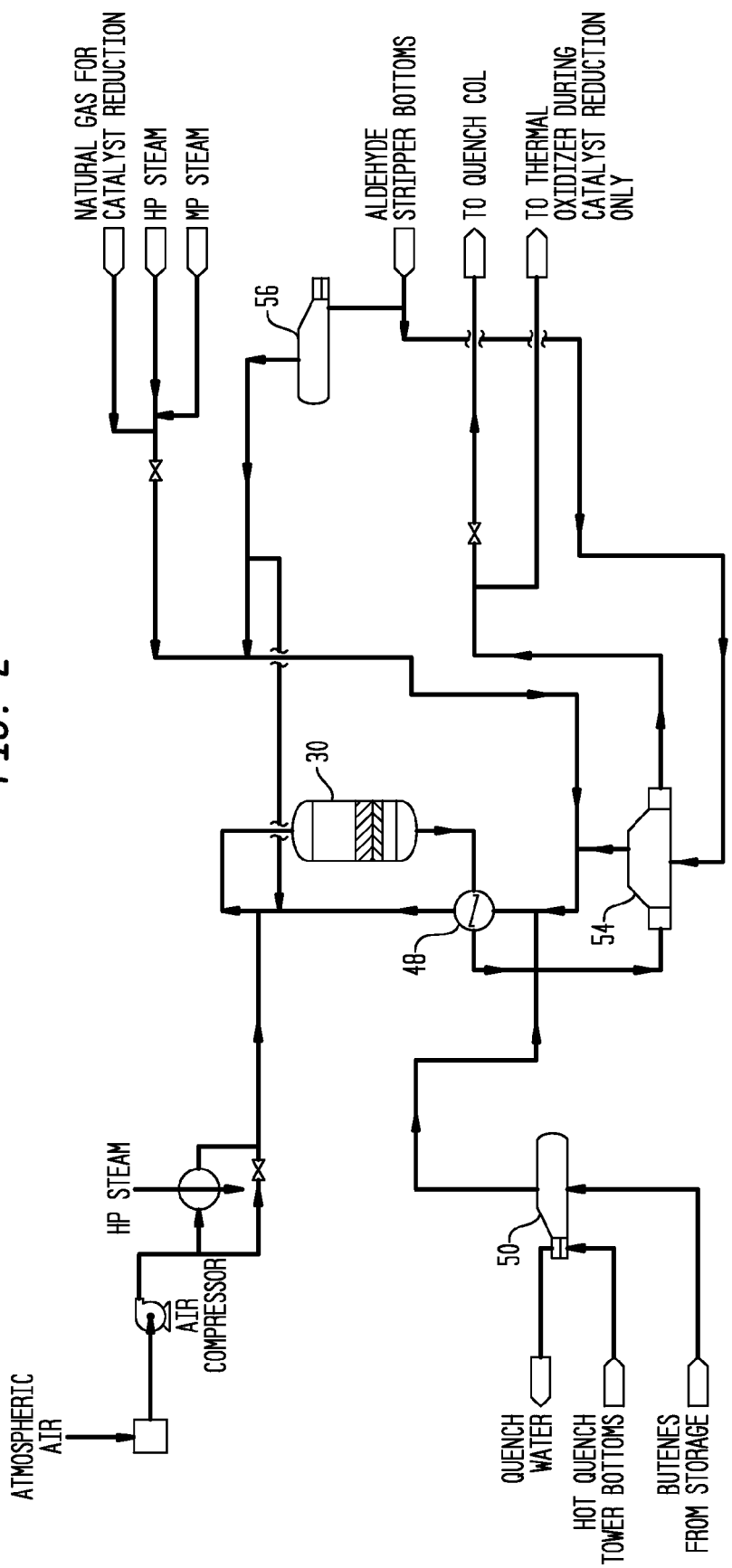
FIG. 2 is a flow diagram of the reactor section of a crude butadiene battery illustrating the reactor and the pretreatment equipment for bringing the butene rich feed to the entry conditions required for operation of the reactor.

In FIG. 2, butene rich feed is vaporized in butene vaporizer 50 in which the heat required for vaporization is supplied by removal of heat from bottoms of quench tower 64 which, as will be discussed later, is heated by contact with the hot reaction product once a steady state operation has been achieve in the current process. After passing through butene vaporizer 50, the vaporized butene feed is mixed with steam, the steam being generated in two recycle condensate vaporizers 54 and 56. The steam generated in recycle condensate vaporizer 54 is produced by indirect heat exchange with butadiene enriched product stream leaving reactor feed superheater 48. The heat required to generate the steam in recycle condensate vaporizer 56 is preferably supplied by steam either from the plant grid or preferably from the thermal oxidizer or some other conveniently available source. Preferably, the steam is completely vaporized in recycle condensate vaporizer 56 prior to being mixed with vaporized butene before passage through reactor feed superheater 48 in which the reactor feed is preheated by indirect heat exchange with the butadiene enriched product stream exiting reactor 30 with the resultant combined entry stream having a temperature of at least about 345° C. (about 650° F.), preferably in the range of from about 345° C. to 400° C. (from about 650° F. to 750° F.). Thus the feed to reactor 30 is heated to the required temperature by indirect heat exchange with the exit stream which, as will be discussed later, is usually at a temperature in excess of 535° C. (1000° F.), more typically around 595° C. (1100° F.). Significantly, the recovered heat passes through only a single tube wall in contrast to schemes in which an intermediate fluid is used. Preheated reactor feed leaving the reactor feed superheater 48 is mixed with compressed oxygen bearing gas, typically air, with the amount of air feed being carefully controlled so that approximately 0.5 to 0.6 moles of oxygen are supplied for each mole of hydrocarbon in the feed passed to the reactors. In some cases, it will be convenient to preheat the oxygen bearing gas to from about 205 to about 235° C. (about 400 to about 450° F.) using high pressure steam. After mixing, the reaction feed stream is passed to refractory lined adiabatic reactor 30 illustrated in FIG. 1, where butene/steam/air feed inside reactor 30 passes first through: an inert flow distribution layer 32 then to an oxidative-dehydrogenation catalyst layer 34, having a depth of 83.8 cm (33 inches) or so; an aldehyde and acetylene removal (AAR) catalyst layer 36 and an inert support (alumina spheres) layer 38.

Further details of the preferred reactor 30 and method of operating it are provided in U.S. Provisional Patent Application Ser. No. 61/617,535, entitled, "IMPROVED CONTROLLABILITY OXIDATIVE DEHYDROGENATION PROCESS FOR PRODUCING BUTADIENE", filed Mar. 29, 2012. It is desired that the catalyst particles used in connection with the present invention be slightly larger than commonly used in previous practice to limit the pressure drop through the catalyst bed as we prefer to use a catalyst bed which is deeper than commonly used previously. Higher pressure drop requires higher pressure in the system which reduces selectivity. We also prefer to use catalyst particles having two key differences from previous practice: (1) the particles are "pre-reduced" or otherwise heat treated prior to loading to give them the crush strength necessary to be usable in a bed having a depth of from about 50 cm to about 150 cm (from about 20" up to about 60"), preferably a depth of from about 65 cm to about 130 cm (from about 25" to about 50"), more preferably from about 75 cm to about 100 cm (from about 30" to about 40"); while the bulk density of the calcined particles is no more than about 1100 kg/m$^3$ (about 70 lbs/ft$^3$), preferably between about 880 kg/m$^3$ and 1050 kg/m$^3$ (about 55 lbs/ft$^3$ and 65 lbs/ft$^3$) and still more preferably is between about 920 kg/m$^3$ and 1010 kg/m$^3$ (about 58 lbs/ft$^3$ and 63 lbs/ft$^3$) and (2) we prefer to avoid the use of nitrates that are conventionally used as precursors for the calcium compounds often incorporated into these catalysts. We have found that calcium acetate is a suitable precursor in this regard and has the advantage of reducing NOx emissions, while calcium chloride and calcium carbonate are also suitable.

Flow distribution is also important for avoiding channeling and hot spots in the catalyst bed. The preferred flow regime is fully turbulent and is enhanced by the presence of the inlet distributor. That is, an inlet distributor is advantageously provided to insure uniform flow distribution through the catalyst bed and prevent channeling and the potential creation of hot spots, which are likely to shorten the catalyst life. One preferred design for this inlet distributor device is in the form of baffles and rings which is mounted in the vapor space above the catalyst bed to promote even distribution of flow and to minimize inlet pressure losses.

Suitable catalysts are also described in Miklas, METHOD OF ACTIVATING ZINC-FERRITE OXIDATIVE DEHYDROGENATION CATALYST; U.S. Pat. No. 3,953,370; Apr. 27, 1976, which relates to use of steam at a temperature of from 371-704° C. (700-1300° F.) to activate a zinc ferrite oxidative dehydrogenation catalyst for preparation of butadiene from $C_4$-$C_8$ hydrocarbons as well as Bajars et al; DEHYDROGENATION WITH MAGNESIUM FERRITE; U.S. Pat. No. 3,284,536; U.S. Pat. No. 4,083,844 to Purdy entitled CALCIUM OXIDE MODIFIED ZINC FERRITE OXIDATIVE DEHYDROGENATION CATALYSTS AND USE as well as CATALYTIC OXIDATIVE DEHYDROGENATION PROCESS; U.S. Pat. No. 4,658,074, the disclosures of which are incorporated herein by reference. Acetylene and aldehyde (AAR) removal catalysts and their usage are described in pending Application No. PCT/US2011/000624, the disclosure of which is also incorporated by reference.

In reactor 30, butenes react with oxygen in a series of reactions ultimately producing a stream in which there is very little, if any, oxygen but a greatly increased concentration of butadiene and greatly reduced amounts of butenes. The reaction product also comprises contaminants which would greatly interfere with use of the butadiene as a feed to a polymerization process if not removed as described hereinafter. Since the reactions occurring in reactor 30 are intensely exothermic, the stream leaving reactor 30 is at a quite elevated temperature usually in excess of 540° C. (1000° F.), more typically closer to 595° C. (1100° F.). By judiciously transferring much of the sensible heat in the stream leaving reactor 30 to portions of the streams being combined to form the feed to reactor 30, it is possible to not only improve the process economics but also to greatly reduce if not eliminate use of natural gas during steady operation. When combined with other means of recovering energy discussed herein, it becomes possible to vaporize and superheat the feed stream to the butene conversion section of the process largely without consumption of energy other than that inherently supplied in the stream of hydrocarbons used to produce the butene rich feed to the process.

The location of the intensely exothermic reaction occurring in each reactor is monitored through a number of remotely readable thermocouples 40 spaced along the height of oxidation-dehydrogenation layer 34 so that the location of the reaction zone therein may be determined as hereinafter described. The amount of oxygen remaining in the product stream is monitored with oxygen analyzer 42 located near the bottom of layer 34 so that oxygen breakthrough into AAR layer 36 is avoided as discussed hereinafter in more detail. Also provided is a lower sample port 44 for a convergence analyzer in layer 36 so that composition may be monitored at the lower extreme of the reactor.

As mentioned previously, the hot reaction product stream from reactor 30 passes through reactor feed superheater 48 (FIG. 2) which supplies a portion of the heat used to bring the feed to reactor 30 up to the requisite operating temperature and thence the reaction product exiting reactor feed superheater 48 passes through steam generator 54 wherein a portion of the sensible heat contained therein is used to vaporize and/or superheat the steam passing to reactor 30.

Figure 3:
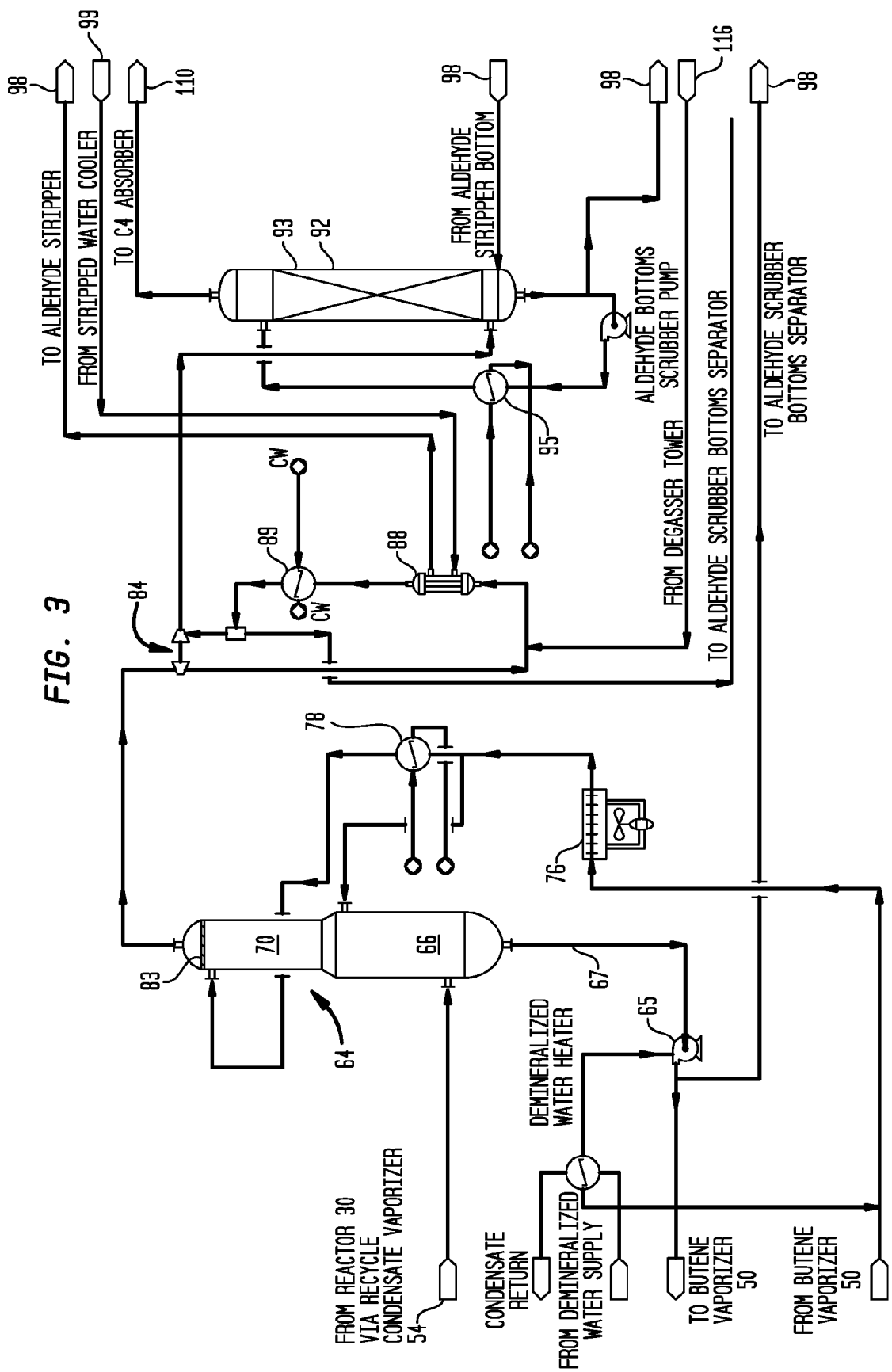
FIG. 3 is a flow diagram of a portion of a crude butadiene battery illustrating the Gas Compressing and Scrubbing equipment for initial processing of a butadiene enriched product stream produced by the reactor section of FIG. 2.

Subsequently, butadiene enriched reaction product exiting from steam generator 54 passes to quench tower 64 (FIG. 3) entering at a height slightly above the maximum liquid level expected during normal operation. As mentioned, in our preferred embodiment, butadiene enriched product stream from reactor 30 is combined with other butadiene enriched product streams from the other reactors (not shown) prior to entering quench tower 64. In one embodiment, bottom section 66 of quench tower 64 is equipped with valve trays while top section 70 is equipped with a corrugated metallic structured packing such as Koch Flexipac®, similar to that described in Lantz, et al., U.S. Pat. No. 6,874,769, Structured Packing Plate and Element and Method of Fabricating Same or Rukovena, U.S. Pat. No. 4,740,334. Alternatively, spray nozzles may be used for the entire tower. It is anticipated that in many cases, it will be possible to feed the mixture of vaporous and liquid reaction product effluent directly into quench tower 64 without any preliminary phase separation; but such preliminary phase separation can be easily accommodated, if expedient, by incorporation of a flash tank or similar phase separation device. The condensate liquid phase collected at lower exit 67 of quench tower 64 comprising primarily of condensed steam and quench water is fed back through the hot side of butene vaporizer 50 with cooled liquid return being passed back via quench condensate air cooler 76 and thence to quench tower circulating cooler 78 before being fed into quench tower 64 at a location well above the top of the packed section 70 of quench tower 64 but below demister pad 83. Preferably quench condensate air cooler 76 is equipped with modular tube banks, individually controlled fans, and variable pitch fan blades to facilitate temperature control in a variety of ambient conditions. In many cases, it will be possible to extract additional heat from Quench Tower bottoms stream 64 for uses elsewhere in the associated plant reducing size and cost of Quench Tower Coolers 76 and 78.

Figure 4:
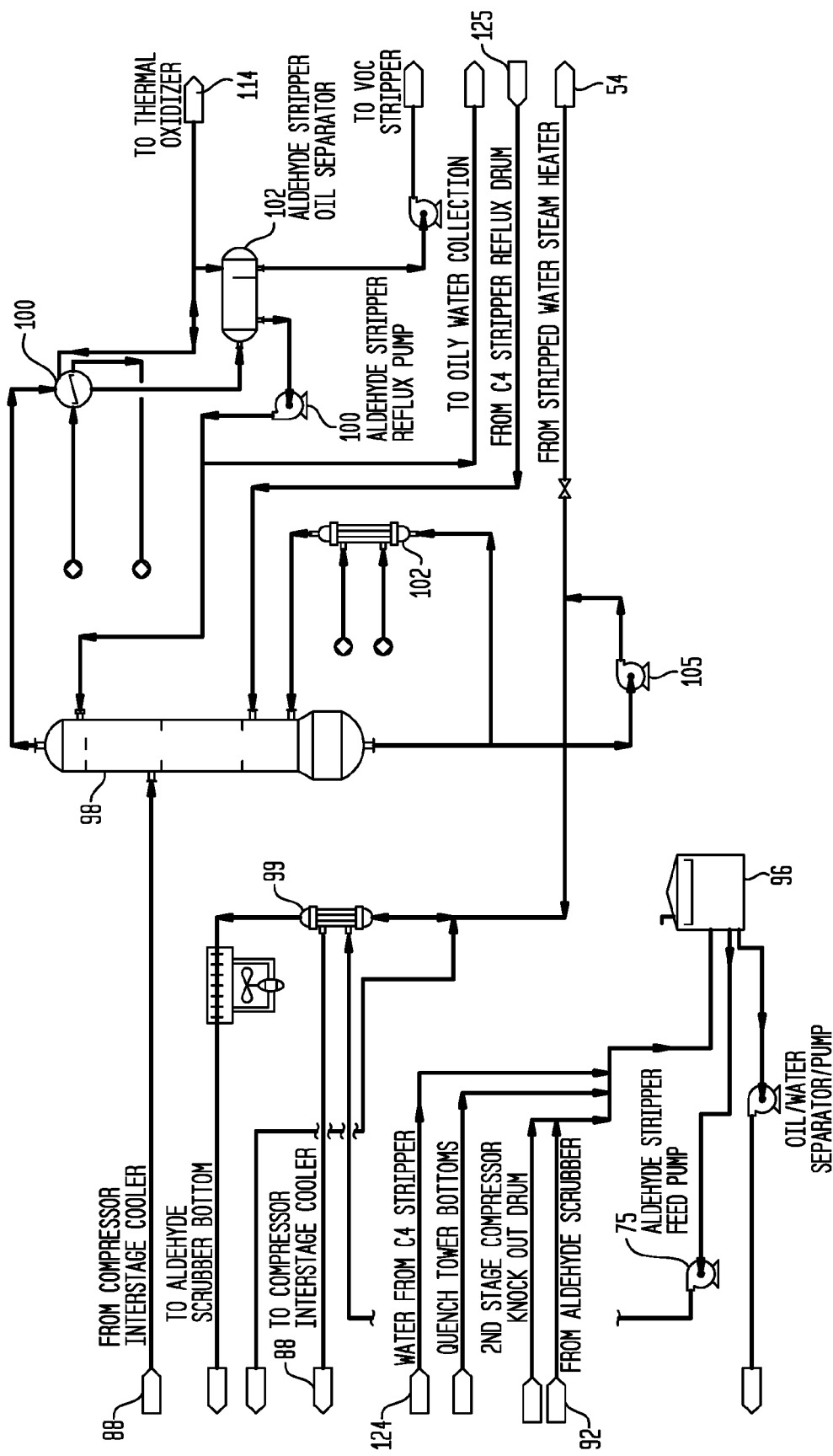
FIG. 4 is a flow diagram of a portion of a crude butadiene battery illustrating the aldehyde stripper and associated equipment for processing of a butadiene enriched product stream after processing by the Gas Compressing and Scrubbing section of FIG. 3.

Crude butadiene vapor leaves top section 70 of quench tower 64 (FIG. 3) passing through demister pad 83, which is included primarily to protect gas compressor 84 from any entrained liquid droplets, and enters on the suction side of two-stage centrifugal gas compressor 84. Indirect inter-stage cooling is provided by compressor inter-stage coolers 88 and 89 with cooling to compressor inter-stage cooler 88 being supplied by a process stream leaving stripped water cooler 99 and the heated stream from the shell side of compressor inter-stage cooler 88 being fed to aldehyde stripper 98 (FIG. 4). Cooling to inter-stage cooler 89 is conveniently supplied by plant cooling tower water.

Entrained liquid droplets coalesced on demister pad 83 are refluxed through quench tower 64 while compressed vaporous butadiene enriched product compressed to 1140 kPa abs. (about 150 psig) leaves the second stage of the gas compressor and it is passed to aldehyde scrubber 92 of which top portion 93 is preferably packed with structured packing which may be similar to Norton Intallox structured packing or those packings described above. A portion of the bottoms from aldehyde scrubber 92 is recycled through the structured packing via aldehyde scrubber bottoms cooler 95 while the remainder is passed to aldehyde stripper 98 via aldehyde scrubber bottoms separator 96 (FIG. 4) which receives liquid from the quench tower 64 bottoms via quench tower bottoms pump 65 as well as from gas compressor 84 second stage knock out drum. The water contents of the aldehyde scrubber bottoms separator 96 may be returned to quench tower 64 at a location below demister pad 83. It is an important aspect of this invention that in those cases where substantial amounts of hydrocarbons lighter than C4 or other low value volatiles can be removed from various streams herein, those off gases are fed to a thermal oxidizer where they are combusted to produce steam which can be used to supply heat as needed for various portions of the overall process thereby greatly reducing need for natural gas combustion in steady operation and thereby also reducing concomitant generation of carbon monoxide and carbon dioxide.

Aldehyde stripper (FIG. 4) receives the water phase from the aldehyde scrubber bottoms after the oil phase has been skimmed out. This stream is pumped first to the shell side of stripped water cooler 99, from whence it reaches the shell side of compressor interstage cooler 88, which helps to increase its temperature via heat integration before being fed to aldehyde stripper 98, a portion of this overhead vapor from aldehyde stripper 98 going to aldehyde stripper overhead condenser 100 and thence being returned to aldehyde stripper 98 as reflux to maintain the vapor/liquid equilibrium in the column and drive overhead the aldehydes contained in the feed to this tower 98. The balance of the overhead vapor stream from aldehyde stripper 98 bypassing overhead condenser 100 is combined with other low value combustibles and directed to a thermal oxidizer (not shown) for production of superheated steam. Heavier hydrocarbons entrained in the condensed overhead stream from overhead condenser 100 are collected by bottoms coalescer and are also disposed of by treatment at a conventional oily water facility (not shown). Aldehyde stripper reboiler 102 uses steam, advantageously medium pressure steam, to vaporize a portion of aldehyde stripper bottoms from aldehyde stripper 98 and reintroduces the vapor below bottom tray of aldehyde stripper 98 while the remainder is pumped using aldehyde stripper bottoms pump 105 to two locations: (1) back to the aldehyde scrubber 92 bottoms below the packing via two stripped water coolers (not shown), and (2) to the recycle condensate vaporizers, where it generates the vast bulk, if not all, of the steam used for the oxidative dehydrogenation reaction.

Figure 5:
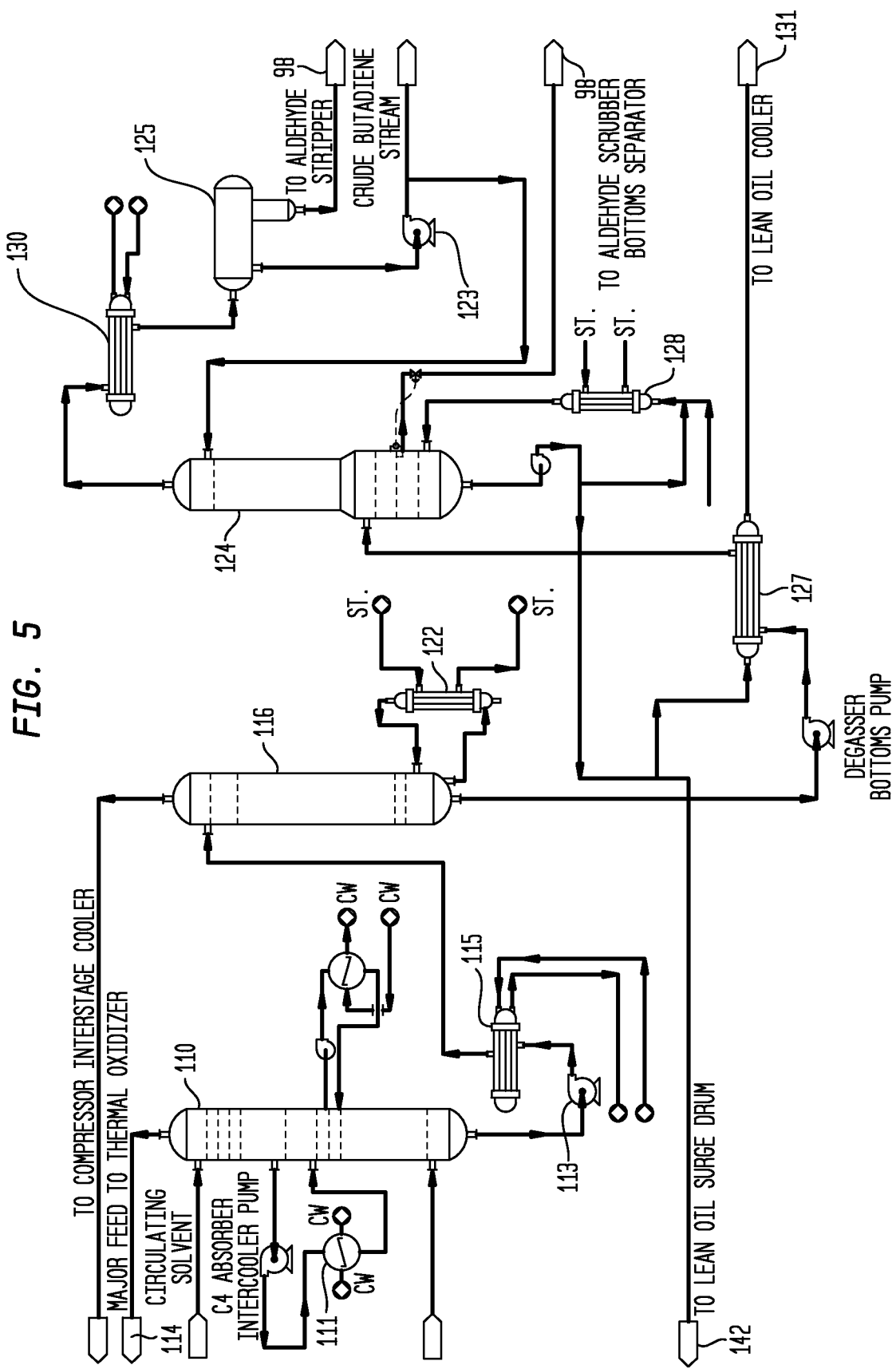
FIG. 5 is a flow diagram of a portion of a crude butadiene battery illustrating the C4 absorption and stripping equipment for production of a crude stream of about 50% butadiene by processing of a butadiene enriched product stream received from the aldehyde stripper section of FIG. 4.

Reaction product from aldehyde scrubber 92 (FIG. 3) overhead is passed to the bottom of C4 absorber 110 (FIG. 5) containing numerous trays or other known devices for promoting gas liquid contact and equipped with at least one intercooler 111. Absorber oil (also sometimes referred to as lean oil) used in absorber 110 can suitably be paraffinic, or a mixture of paraffins and aromatics, although it seems like better results are obtained using oils which are richer in, or possibly even entirely, vinyl cyclohexene (butadiene dimer). Good commercial results have been obtained when the fresh absorber oil is primarily Espersol 250, an aromatic Naphtha product with a boiling range of 90° C. to 150° C. (200° F. to 300° F.) having the composition shown in Table 1 (Celsius Boiling Points provided in Table 1A).

TABLE 1

Absorber Oil Composition

| Component | Molecular Weight | N.B. Point (° F.) | Specific Gravity | Chroma. % | Assumed Wt % | Mole % | Vol. % |
|---|---|---|---|---|---|---|---|
| Benzene | 78.11 | 176.2 | 0.8845 | 6 | 5 | 6.8 | 5 |
| Cyclohexane | 84.16 | 178 | 0.783 | 3 | 2 | 2.5 | 2.3 |
| Methyl Cyclohexane | 98.18 | 213.7 | 0.774 | 1 | 1 | 1.1 | 1.1 |
| Toluene | 92.13 | 231 | 0.872 | 12 | 13 | 15 | 13.2 |
| 2,2,4-Trimethyl Pentane | 114.23 | 236.1 | 0.696 | 1 | 2 | 1.9 | 2.6 |
| Vinyl Cyclohexane | 108.18 | 262.1 | 0.8335 | 3 | 5 | 4.9 | 5.3 |
| Ethyl Cyclohexane | 112.22 | 269.2 | 0.788 | 1 | 1 | 0.9 | 1.1 |
| M&P-Xylene | 106.16 | 281 | 0.867 | 19 | 20 | 20.1 | 20.4 |
| O-Xylene | 106.16 | 291 | 0.885 | 17 | 18 | 18.1 | 18 |
| Styrene | 104.14 | 294 | 0.911 | 10 | 12 | 12.3 | 11.6 |
| Propyl Benzene | 120.19 | 318.6 | 0.862 | 1 | 2 | 1.8 | 2.1 |
| Butyl Benzene | 134.21 | 361.4 | 0.864 | 4 | 6 | 4.8 | 6.1 |
| "Heavies" (Assume 2-M Naphthalene) | 142.2 | 466 | 1.029 | 22 | 13 | 9.7 | 11.2 |

TABLE 1A

Absorber Oil Composition (Celsius Boiling Points)

| Component | Molecular Weight | N.B. Point (° C.) | Specific Gravity | Chroma. % | Assumed Wt % | Mole % | Vol. % |
|---|---|---|---|---|---|---|---|
| Benzene | 78.11 | 80.11 | 0.8845 | 6 | 5 | 6.8 | 5 |
| Cyclohexane | 84.16 | 81.1 | 0.783 | 3 | 2 | 2.5 | 2.3 |
| Methyl Cyclohexane | 98.18 | 100.9 | 0.774 | 1 | 1 | 1.1 | 1.1 |
| Toluene | 92.13 | 111 | 0.872 | 12 | 13 | 15 | 13.2 |
| 2,2,4-Trimethyl Pentane | 114.23 | 113.4 | 0.696 | 1 | 2 | 1.9 | 2.6 |
| Vinyl Cyclohexane | 108.18 | 127.8 | 0.8335 | 3 | 5 | 4.9 | 5.3 |
| Ethyl Cyclohexane | 112.22 | 131.8 | 0.788 | 1 | 1 | 0.9 | 1.1 |
| M&P-Xylene | 106.16 | 138 | 0.867 | 19 | 20 | 20.1 | 20.4 |
| O-Xylene | 106.16 | 144 | 0.885 | 17 | 18 | 18.1 | 18 |
| Styrene | 104.14 | 146 | 0.911 | 10 | 12 | 12.3 | 11.6 |
| Propyl Benzene | 120.19 | 159.2 | 0.862 | 1 | 2 | 1.8 | 2.1 |
| Butyl Benzene | 134.21 | 183 | 0.864 | 4 | 6 | 4.8 | 6.1 |
| "Heavies" (Assume 2-M Naphthalene) | 142.2 | 241 | 1.029 | 22 | 13 | 9.7 | 11.2 |

Butadiene in the product stream is absorbed in absorber oil introduced at the top of C4 absorber 110, the bottoms from which is pumped to the top of degasser tower 116 through C4 absorber bottoms pump 113 and degasser feed cooler 115. Degasser tower 116 operates at lower pressure to facilitate the removal of residual gases, particularly carbon dioxide, nitrogen and hydrogen, which are passed through inter-stage cooler 88 of two-stage gas compressor 84 to the butadiene enriched product stream prior to passage through aldehyde scrubber 92. Degasser overhead gas from degasser 116 is recycled back to the second stage of compressor 84 and thence to scrubber 92 and absorber 110 whence it will ultimately find its way to thermal oxidizer 114. Degasser reboiler 122 maintains the temperature in the liquid phase of degasser tower 116 sufficiently high to allow residual gases to be flashed out passing to thermal oxidizer 114 as described above. The bottoms from degasser tower 116 largely comprising crude butadiene and miscellaneous C4's in absorber oil are passed to C4 stripper 124 through C4 stripper feed bottoms interchanger 127 where this bottoms stream is heated by passage of hot absorber oil from the bottoms of C4 stripper 124 through the tubes of C4 stripper feed/bottoms interchanger 127. Heated degasser bottoms are introduced into C4 stripper 124 at an intermediate height. Crude butadiene and C4's are stripped from heated absorber oil in C4 stripper 124, passing out as overhead to C4 stripper overhead condenser 130 while depleted absorber oil collected in the bottoms from C4 stripper 124 is reheated in C4 stripper reboiler 128; and the overhead vapor from C4 stripper 124 is condensed in C4 stripper overhead condenser 130 with a portion of the condensed liquid being accumulated in C4 stripper reflux drum 125, where residual water can be separated from the hydrocarbon phase and sent back to aldehyde stripper tower 98, while crude butadiene product is pumped through C4 stripper reflux pump 123 to further processing, while sufficient crude butadiene is being recirculated as reflux to ensure that sufficient separation is attained in C4 stripper 124.

Figure 6:
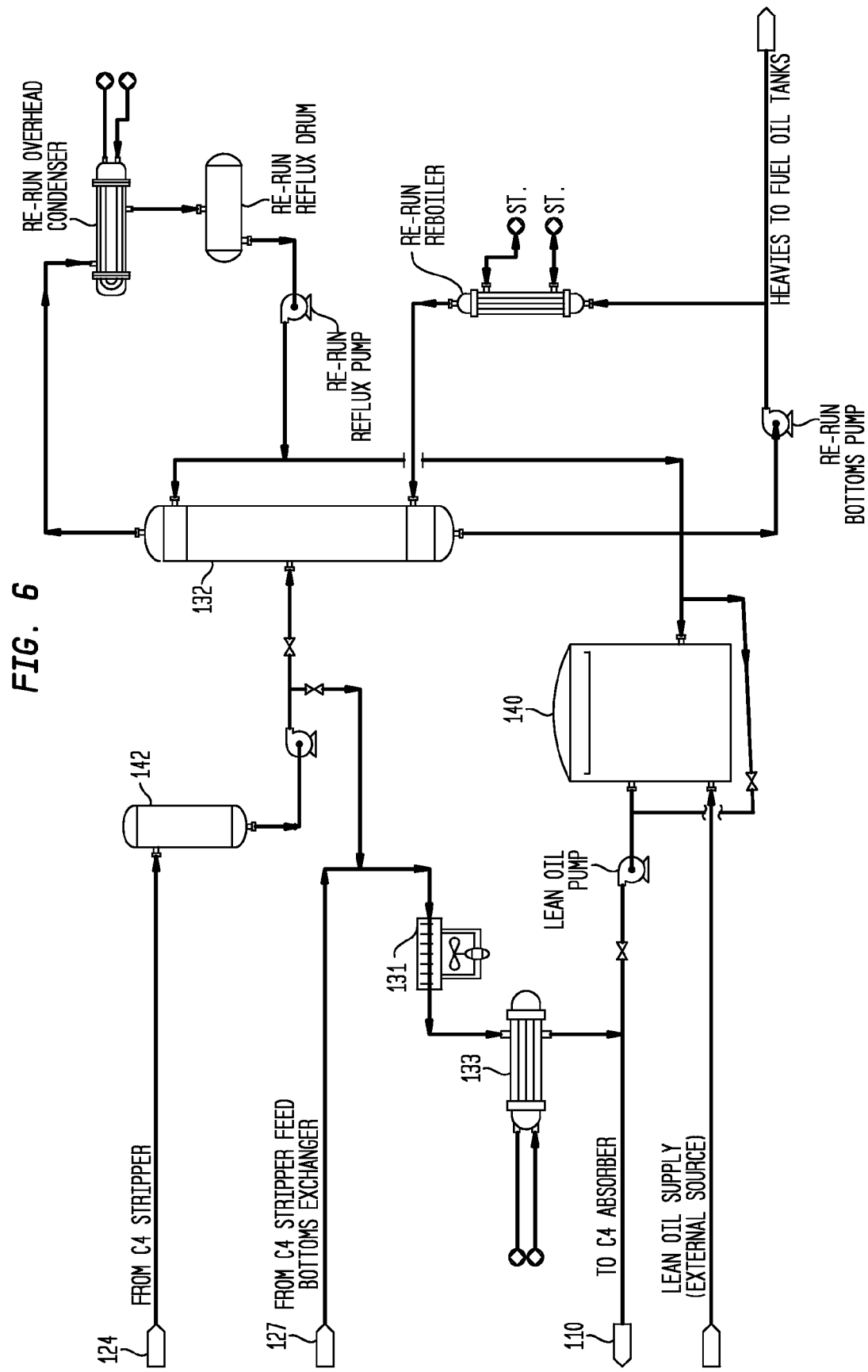
FIG. 6 is a flow diagram of a portion of a crude butadiene battery illustrating portions of the system used for handling of absorption oil after stripping of C4's therefrom.

Bottoms leaving C4 stripper 124 comprise absorber oil having butadiene and other C4s stripped therefrom which is divided into three portions, one of which is recirculated to C4 stripper 124 through C4 stripper reboiler 128, a second portion being passed to absorber oil surge drum 142, (FIG. 6) the remaining portion being used as mentioned previously to heat butadiene/absorption oil mixture upon passage through C4 stripper feed/bottoms interchanger 127 where it, and oil being recycled from absorption oil surge drum 142, are passed to absorption oil air cooler 131 and absorption oil cooler 133 before being returned to C4 absorber 110 for reuse. As absorber oil breaks down, forming heavier molecules, fresh oil make-up is introduced into the system while the balance is directed to a re-run column for heavies cleanup. Upon sufficient accumulation of heavies in the absorption oil to justify, or necessitate, operation of absorber oil re-run tower 132, a portion of the oil being recirculated from absorption oil surge drum 142 is distilled to remove heavier components in absorber oil re-run tower bottoms with the overhead being pumped back to absorber oil recirculation loop. Occasionally the recovered oil could be pumped to storage tank 140 where the fresh absorber oil is stored.

Tables 2 and 2A sets forth an energy balance for three possible plant configurations for 23,000 kg/hr (50,600 lb/hr) of butadiene production: one having no thermal oxidizer; one having a small thermal oxidizer sized primarily for the low value combustibles produced in the process of converting butene to butadiene; and one sized for both the low value combustibles produced in the process of converting butene to butadiene as well as those produced in the process of purifying crude butadiene to a saleable grade. It can be appreciated that the energy requirement for vaporizing and superheating the various streams fed to the reactor during steady operation of the process for converting butenes to butadiene is surprisingly small when sensible heat in the reaction product stream is combined with the energy resulting from thermal oxidation of low value combustibles from both butadiene production and purification.

TABLE 2

Low Emissions/Heat Integration for Oxidative Dehydrogenation of Butene

| | |
|---|---|
| BD Production: | 50,600 LB/HR |
| Total Energy† Required: | 432,112,000 BTU/HR |
| Energy provided by Sensible Heat in Butadiene Enriched Product Stream (BTU/HR) | |
| Butene Vaporizer 50 | 14,558,000 |
| Superheater 48 (Butene) | — |
| Superheater 48 (Steam) | 95,783,000 |
| Condensate Vaporizer 54 | 11,613,000 |
| SubTotal† | 221,954,000 |
| Additional Energy Required to Vaporize Steam for Reactor Feed (BTU/HR) * | |
| Condensate Vaporizer 56 | 210,159,000 |

| Thermal Oxidizer Size: | Energy Contribution from Combustion of By-Products (Supplied via Steam) | % Energy from Process Sources | % Energy from Fossil Fuel | Lbs. of NG required for each lb of Butadiene Produced | % Energy for Vaporizing Recycle Condensate and Super-heating Feed from Thermal Oxidizer | % Energy for Vaporizing Recycle Condensate and Super-heating Feed from Reactor Effluent |
|---|---|---|---|---|---|---|
| none | 0 | 51 | 48 | 0.20 | — | 51 |
| offgases from Crude BD production only | 150,000 #/hr 150# Steam | 61 | 39 | 0.16 | 10 | 51 |

TABLE 2-continued

| Offgases from production and purification of Crude BD | 250,000 #/hr 150# Steam | 91 | 9 | 0.04 | 40 | 51 |

* Energy calculated based on 150# superheated steam @ 810° F. generated by combination of thermal oxidation of by-products from butene and butadiene production as supplemented by combustion of natural gas at 21,000 BTU/LB as fuel for steam boiler to produce 1112 BTU/LB of Steam during first phase of steady operation
†Totals do not agree perfectly due to rounding.

TABLE 2A (Metric Units)

Low Emissions/Heat Integration for Oxidative Dehydrogenation of Butene

| BD Production: | 23,000 kg/HR |
| Total Energy† Required: | 455,597,000 kJ/HR |

Energy provided by Sensible Heat in Butadiene Enriched Product Stream (kJ/HR)

| Butene Vaporizer 50 | 15,349,000 |
| Superheater 48 (Butene) | — |
| Superheater 48 (Steam) | 100,988,000 |
| Condensate Vaporizer 54 | 117,679,100 |
| SubTotal† | 234,017,000 |

Additional Energy Required to Vaporize Steam for Reactor Feed (kJ/HR) *

| Condensate Vaporizer 56 | 221,581,000 |

| Thermal Oxidizer Size: | Energy Contribution from Combustion of By-Products (Supplied via Steam) | % Energy from Process Sources | % Energy from Fossil fuel | kg. of NG required for each kg of Butadiene Produced | % Energy for Vaporizing Recycle Condensate and Superheating Feed from Thermal Oxidizer | % Energy for Vaporizing Recycle Condensate and Superheating Feed from Reactor Effluent |
|---|---|---|---|---|---|---|
| none | 0 | 51 | 48 | 0.20 | — | 51 |
| offgases from Crude BD production only | 68,039 kg/hr 1.034 MPa Steam | 61 | 39 | 0.16 | 10 | 51 |
| Offgases from production and purification of Crude BD | 113,398 kg/hr 1.034 MPa Steam | 91 | 9 | 0.04 | 40 | 51 |

* Energy calculated based on 68.0 kg superheated steam @ 432° C. generated by combination of thermal oxidation of by-products from butene and butadiene production as supplemented by combustion of natural gas at 48,813 kJ/kg as fuel for steam boiler to produce 2585 kJ/kg of Steam during first phase of steady operation Energy requirements for the reaction section can also be expressed in kJ/kg (BTU/LB) BD (butadiene) produced as set forth in Tables 3 and 3A below.

TABLE 3

Reaction Section Energy Utilization

| Total Energy required*: | 8540 BTU/LB BD |
| Energy for Superheater 48 | 1890 BTU/LB BD |
| Energy for Vaporizer 50 | 288 BTU/LB BD |
| Energy for Vaporizer 54 | 2200 BTU/LB BD |
| Energy for Vaporizer 56 | 4150 BTU/LB BD |

*Approx. values

TABLE 3A

Metric Units

| Total Energy required*: | 19,900 kJ/kg BD |
| Energy for Superheater 48 | 4,400 kJ/kg BD |
| Energy for Vaporizer 50 | 670 kJ/kg BD |
| Energy for Vaporizer 54 | 5,130 kJ/kg BD |
| Energy for Vaporizer 56 | 9,650 kJ/kg BD |

*Approx. values

The data in Tables 2, 2A, 3 and 3A reflects process modeling using fresh catalyst.

All of the energy for Superheater 48, over 4400 kJ/kg (1900 BTU per pound) of butadiene, may be supplied by indirect heat transfer of sensible heat from the reactor effluent stream at high temperature, with the effluent product stream well above 370° C. (700° F.). Likewise, all of the energy for vaporizer 54 may similarly be supplied by indirect heat transfer at a somewhat lower temperature of the effluent product stream. Heat recovery from the process stream is enhanced by extracting heat from the effluent stream when the stream is at a relatively high temperature for purposes of superheating the feed and then extracting heat from the reactor effluent at a relatively lower temperature for purposes of vaporizing feed. Energy for vaporizer 56 may be supplied from a plant steam grid which draws heat from thermal oxidation of volatile organic compounds generated in connection with the oxidative dehydration process as described herein.

In preferred embodiments, the vaporized and superheated hydrocarbonaceous butene rich feed is brought to a temperature of at least about 205° C. (about 400° F.), more preferably 260° C. (500° F.), still more preferably at least about 315° C. (about 600° F.), most preferably about 345° C. (about 650° F.), mixed with hydrocarbonaceous butene rich feed, superheated steam and an oxygen rich gas to form a reactor feed stream and the moles of oxygen in said reactor feed stream being controlled to fall in the range of at least about 0.4 moles, more preferably at least about 0.5 moles and most preferably about 0.55 moles of oxygen per mole of hydrocarbonaceous butene rich feed.

Preferably the feed mixture comprising butenes, steam, and oxygen is oxidatively dehydrogenated over a ferritic oxide catalyst consisting essentially of: oxygen, a major proportion of iron; a minor proportion of zinc; and smaller amounts of manganese; phosphorus, with the residue of a nitrate free calcium precursor, thereby forming a butadiene enriched product stream. The use of substantially nitrate free oxidative dehydrogenation catalyst is extremely advantageous.

The energy content of the butadiene enriched product stream is used to provide heat for the reaction feed stream by a combination of indirect heat exchange to remove sensible heat from the butadiene enriched product stream and thermal oxidation of undesired hydrocarbonaceous products separated from the butadiene enriched product stream by first passing the butadiene enriched product stream through a reactor feed superheater in which a mixture of steam and butene enriched hydrocarbons entering the reactor is superheated by indirect heat exchange with said butadiene enriched product stream to a temperature of at least 205° C. (400° F.), preferably at least 260° C. (500° F.), more preferably at least about 315° C. (about 600° F.) and most preferably to about 345° C. (about 650° F.);

Subsequently, the butadiene enriched product stream is next passed through a steam generator in which water, preferably water condensed from the process stream, is vaporized by indirect heat exchange with the butadiene enriched product stream.

The butadiene enriched product stream is subsequently quenched is a quench tower, compressed, scrubbed to remove aldehydes and passed through a C4 absorber wherein C4 species including butadiene are absorbed in an absorption oil which is sometimes also referred to as lean oil.

The butadiene is recovered by passing the absorption oils through a degasser tower in which non-C4 volatiles are removed; a C4 stripper in which C4's including butadiene are desorbed or stripped from said absorption oil under reduced pressure. Preferably, dispersed volatile lower organics are stripped from the liquid stripped from the butadiene enriched product stream and the resultant aqueous stream is recycled to the steam generator while the volatile organics are oxidized to generate steam used to supply the heat required to vaporize water supplied to the steam generator.

Thermal oxidation of low value products recovered from (1) the butadiene enriched product stream, and (2) by-products of the purification of crude butadiene into the salable butadiene generates sufficient heat so that in steady operation, the energy content of the feed to the oxidative dehydrogenation process supplies at least 60%, preferably 70% and more preferably 85% of the energy required for (1) vaporizing and superheating said hydrocarbonaceous butene rich feed; and (2) vaporizing and superheating the water used to supply said superheated steam in said reactor feed stream during steady operation in the production cycle.

In our preferred processes, for each kg of butadiene produced, less than 0.15 kg, more preferably less than 0.10 kg, most preferably less than 0.05 kg of natural gas is consumed in (a) vaporizing and superheating the butene rich feed and (b) vaporizing and superheating the water used to supply the superheated steam in said reactor feed stream as the energy required therefore is supplied by the energy content of the butene rich feed to the oxidative dehydrogenation process.

By thermal oxidation of dispersed volatile lower organics removed from the butadiene enriched product stream at various stages of the process during steady operation, it is possible to recover sufficient energy in steady operation that the total heat required to both vaporize and superheat the butene rich feed as well as to vaporize and superheat the water used to supply the superheated steam supplied to the reactor feed stream is no more than 130%, preferably no more than 110% of the sum of (1) the sensible heat extracted from the butadiene enriched product stream and (2) the heat generated by thermal oxidation of (a) undesired products removed from the butadiene enriched product stream, and (b) by-products of the conversion of alkanes into the butenes enriched stream supplying the butene rich feed.

In preferred configurations, at least 75% of the heat required to vaporize the water stripped from the butadiene enriched product stream is supplied by a combination of: (1) sensible heat in said butadiene enriched product stream; (2) thermal oxidation of undesired volatiles from the butadiene enriched product stream.

More preferably, at least about 50% the heat required to vaporize the water stripped from the butadiene enriched product stream is supplied by:
(a) sensible heat in said butadiene enriched product stream;
(b) heat obtained from thermal oxidation of undesired volatile products obtained from the butadiene enriched product stream.

Even more preferably, at least about 75% of the energy required to vaporize and superheat said hydrocarbonaceous butene rich feed; and superheat the water used to supply said superheated steam in said reactor feed stream is supplied by the energy content of said butene rich feed to the oxidative dehydrogenation process.

The present invention includes the improvement comprising:
(a) reacting said butene rich feed stream in an oxidative dehydrogenation reactor to form a butadiene enriched product effluent stream which exits said reactor at an elevated temperature;
(b) feeding said butadiene enriched product effluent stream to a feed superheater, wherein the butadiene enriched product effluent stream is provided to the superheater at a temperature of 425° C. (800° F.) or more, reactor feed also being provided to the superheater;
(c) superheating reactor feed in the superheater to a temperature of at least 260° C. (500° F.) with indirect heat transfer of sensible heat from the butadiene enriched product effluent stream to the feed;
(d) subsequent to step (c), feeding the butadiene enriched product effluent stream exiting the superheater to a feed vaporizer, wherein the butadiene enriched product effluent stream entering the vaporizer is at a temperature of at least 205° C. (400° F.); and (e) vaporizing feed in the vaporizer with indirect heat transfer of sensible heat from the butadiene enriched product effluent stream to the feed. Generally, the butadiene enriched product effluent stream is provided to the superheater at a temperature of 485° C. (900° F.) or more; typically the butadiene enriched product effluent stream is provided to the superheater at a temperature of 540° C. (1000° F.) or more; and preferably the butadiene enriched product effluent stream is provided to the superheater at a temperature of 595° C. (1100° F.) or more. In most cases the butadiene enriched product effluent stream is provided to the superheater at a temperature of from 480° C. to 760° C. (900° F. to 1400° F.). The butadiene enriched product effluent stream is generally provided to the vaporizer at a temperature of at least 290° C. (550° F.) such as wherein the butadiene enriched product effluent stream is provided to the vaporizer at a temperature of at least 315° C. (600° F.) or wherein the butadiene enriched product stream is provided to the vaporizer at a temperature of at least 345° C. (650° F.). The butadiene enriched product stream is usually provided to the vaporizer at a temperature of from 260° C. to 425° C. (500° F. to 800° F.).

In accordance with the improved process, the feed is generally heated in the superheater to a temperature of at least 290° C. (550° F.) such as wherein feed is heated in the superheater to a temperature of at least 316° C. (600° F.) or wherein feed is heated in the superheater to a temperature of at least 345° C. (650° F.); usually the feed is heated in the superheater to a temperature of from 260° C. to 485° C. (500° F. to 900° F.). Under typical operating conditions, the temperature delta of the butadiene enriched product effluent stream through the superheater is at least 120° C. (220° F.) such as wherein the temperature delta of the butadiene enriched product effluent stream through the superheater is at least 150° C. (270° F.) or wherein the temperature delta of the butadiene enriched product effluent stream through the superheater is at least 180° C. (325° F.). In most cases the temperature delta of the butadiene enriched product effluent stream through the superheater is from 120° C. to 235° C. (220° F. to 425° F.).

In accordance with the improved process of the invention, in typical operation, at least 2300 kJ/kg (1000 BTU/LB) BD produced is transferred from the butadiene enriched product effluent stream to feed in the superheater by indirect heat exchange such as wherein at least 3500 kJ/kg (1500 BTU/LB) BD produced is transferred from the butadiene enriched product effluent stream to feed in the superheater by indirect heat exchange. Likewise, typically at least 2300 kJ/kg (1000 BTU/LB) BD produced is transferred from the butadiene enriched product stream to feed in the vaporizer by indirect heat exchange such as wherein at least 3500 kJ/kg (1500 BTU/LB) BD produced is transferred from the butadiene enriched product stream to feed in the vaporizer by indirect heat exchange or wherein at least 4100 kJ/kg (1750 BTU/LB) BD produced is transferred from the butadiene enriched product stream to feed in the vaporizer by indirect heat exchange. Under most typical conditions, from 2300 to 5800 kJ/kg (1000 to 2500 BTU/LB) BD produced is transferred from the butadiene enriched product effluent stream to feed in the superheater by indirect heat exchange and from 2300 to 7000 kJ/kg (1000 to 3000 BTU/LB) BD produced is transferred from the butadiene enriched product stream to feed in the vaporizer by indirect heat exchange.

In another aspect of the invention, there is provided an apparatus for producing butadiene by way of oxidative dehydrogenation of a butane-rich feed stream comprising:

(a) a reactor adapted for receiving said butane-rich feed stream and converting butenes to butadiene by oxidative dehydrogenation, thereby providing a butadiene enriched product effluent stream which exits the reactor at an elevated temperature;

(b) a superheater coupled to the reactor to receive the butadiene enriched product effluent stream from the reactor at elevated temperature as well as being configured to receive reactor feed, said superheater being adapted to transfer sensible heat from the butadiene enriched product effluent stream to reactor feed and provide superheated feed to the reactor;

(c) a first vaporizer coupled to the reactor to receive the butadiene enriched product effluent stream as it exits the superheater and to transfer sensible heat from the butadiene enriched product effluent stream to reactor feed;

(d) a second vaporizer coupled to the reactor for providing vapor feed thereto;

(e) a purification train for recovering butadiene from the butadiene enriched product effluent stream; and (f) a thermal oxidizer for recovering energy by way of oxidizing by-products from the purification train and providing energy for said second vaporizer. The apparatus is characterized wherein the superheater is adapted to transfer at least 2300 kJ/kg (1000 BTU/LB) BD produced from the butadiene enriched product effluent stream to feed by indirect heat exchange such as wherein the superheater is adapted to transfer at least 3500 kJ/kg (1500 BTU/LB) BD produced from the butadiene enriched product effluent stream to feed by indirect heat exchange. Likewise, the first vaporizer is adapted to transfer at least 2300 kJ/kg (1000 BTU/LB) BD produced from the butadiene enriched product effluent stream to feed by indirect heat exchange such as wherein the first vaporizer is adapted to transfer at least 3500 kJ/kg (1500 BTU/LB) BD produced from the butadiene enriched product effluent stream to feed by indirect heat exchange. In general, the first vaporizer is adapted to transfer at least 4300 kJ/kg (1850 BTU/LB) BD produced from the butadiene enriched product effluent stream to feed by indirect heat exchange.

Typically, the superheater is adapted to transfer from 2300 to 8100 kJ/kg (1000 to 3500 BTU/LB) BD produced from the butadiene enriched product effluent stream to feed by indirect heat exchange and the first vaporizer is adapted to transfer from 2300 to 10,500 kJ/kg (1000 to 4500 BTU/LB) BD produced from the butadiene enriched product effluent stream to feed by indirect heat exchange.

The thermal oxidizer is adapted to provide at least 930 kJ/kg (400 BTU/LB) BD produced to said second vaporizer and in most cases the thermal oxidizer is adapted to provide at least 1800 kJ/kg (800 BTU/LB) BD produced to said second vaporizer. More preferably, the thermal oxidizer is adapted to provide at least 3700 kJ/kg (1600 BTU/LB) BD produced to said second vaporizer, such as wherein the thermal oxidizer is adapted to provide at least 4600 kJ/kg (2000 BTU/LB) BD produced to said second vaporizer or wherein the thermal oxidizer is adapted to provide at least 6500 kJ/kg (2800 BTU/LB) BD produced to said second vaporizer.

A typical apparatus is configured wherein the superheater is adapted to transfer from 2300 to 8000 kJ/kg (1000 to 3500 BTU/LB) BD produced from the butadiene enriched product effluent stream to feed by indirect heat exchange and the first vaporizer is adapted to transfer from 2300 to 10,500 kJ/kg (1000 to 4500 BTU/LB) BD produced from the butadiene enriched product effluent stream to feed by indirect heat exchange and the thermal oxidizer is adapted to provide at least 930 kJ/kg (400 BTU/LB) BD produced to said second vaporizer such as wherein the superheater is adapted to transfer from 2300 to 8000 kJ/kg (1000 to 3500 BTU/LB) BD produced from the butadiene enriched product effluent stream to feed by indirect heat exchange and the first vaporizer is adapted to transfer from 2300 to 10,500 kJ/kg (1000 to 4500 BTU/LB) BD produced from the butadiene enriched product effluent stream to feed by indirect heat exchange and the thermal oxidizer is adapted to provide at least 4600 kJ/kg (2000 BTU/LB) BD produced to said second vaporizer.

While the invention has been described in detail, modifications within the spirit and scope of the invention will be readily apparent to those of skill in the art. In view of the foregoing discussion, relevant knowledge in the art and references, including co-pending applications, discussed above in connection with the Background and Detailed Description, the disclosures of which are all incorporated herein by reference, further description is deemed unnecessary. In addition, it should be understood that aspects of the invention and portions of various embodiments may be combined or interchanged either in whole or in part. Furthermore, those of ordinary skill in the art will appreciate that the foregoing description is by way of example only, and is not intended to limit the invention.

As our invention, we claim:

1. An improved low emissions method of converting a hydrocarbonaceous butene rich feed into butadiene, wherein the improvement comprises the steps of:
    vaporizing said hydrocarbonaceous butene rich feed, mixing the vaporized hydrocarbonaceous butene rich feed with steam to produce a combined stream, and superheating the combined stream to provide a reactor feed stream;
    oxidatively dehydrogenating said reactor feed stream with an oxygen rich gas over a ferritic catalyst, thereby forming a butadiene enriched product stream, wherein the temperature of the butadiene enriched product stream is at least about 510° C. (950° F.);
    passing the butadiene enriched product stream at a temperature of at least about 510° C. (950° F.) first through a reactor feed superheater in which the reactor feed stream is superheated by indirect heat exchange with said butadiene enriched product stream to at least 345° C. (650° F.);
    passing the butadiene enriched product stream exiting said reactor feed superheater through a steam generator in which water is vaporized by indirect heat exchange with said butadiene enriched product stream exiting said reactor feed superheater to provide vaporized and/or superheated steam;
    passing the butadiene enriched product stream exiting said steam generator through a C4 absorber, wherein C4 compounds including butadiene are absorbed in an absorption oil,
    passing the absorption oil through: (i) a degasser tower in which non-C4 volatiles are removed and (ii) a C4 stripper in which C4 compounds including butadiene are desorbed/stripped from said absorption oil under reduced pressure,
    passing the non-C4 volatiles to a thermal oxidizer to generate steam, wherein the steam from the thermal oxidizer is used to supply heat to the reactor feed stream,
    stripping aqueous liquid from the butadiene enriched product stream to provide an aqueous stream containing dispersed volatile organics,
    stripping the dispersed volatile organics from the aqueous stream to produce a resultant aqueous stream, wherein the resultant aqueous stream is recycled to the steam generator;
    such that in steady operation, the energy content of said butadiene enriched product stream supplies at least 40% of the energy needed for:
    vaporizing and superheating said hydrocarbonaceous butene rich feed; and
    vaporizing and superheating the water used to supply superheated steam in said reactor feed stream.

2. The improved low emissions method of converting a hydrocarbonaceous butene rich feed into butadiene of claim 1, wherein the heat required to vaporize water supplied to the steam generator is supplied at least in part by heat generated by thermal oxidation of the non-C4 volatiles separated from the butadiene enriched product stream.

3. The improved low emissions method of converting a hydrocarbonaceous butene rich feed into butadiene of claim 1, wherein the ferritic catalyst is a ferritic oxide catalyst consisting essentially of: oxygen, a major proportion of iron, a minor proportion of zinc, manganese, phosphorus, and the residue of a nitrate free calcium precursor.

4. The improved low emissions method of converting a hydrocarbonaceous butene rich feed into butadiene of claim 1, wherein during steady operation, the energy content of said butadiene enriched product stream supplies at least 45% of the energy required for:
    vaporizing and superheating said hydrocarbonaceous butene rich feed; and
    vaporizing and superheating the water used to supply superheated steam in said reactor feed stream.

5. The improved low emissions method of converting a hydrocarbonaceous butene rich feed into butadiene of claim 1, wherein during steady operation, the energy content of said butadiene enriched product stream supplies at least 50% of the energy required for:
    vaporizing and superheating said hydrocarbonaceous butene rich feed; and
    vaporizing and superheating the water used to supply superheated steam in said reactor feed stream.

6. The improved low emissions method of converting a hydrocarbonaceous butene rich feed into butadiene of claim 1, wherein the energy content of said butadiene enriched product stream supplies such a proportion of the energy required for:
    (a) vaporizing and superheating said hydrocarbonaceous butene rich feed; and
    (b) vaporizing and superheating the water used to supply superheated steam in said reactor feed stream,
    that less than 0.35 kg of natural gas is consumed in steps (a) and (b) for each kg of butadiene produced.

7. The improved low emissions method of converting a hydrocarbonaceous butene rich feed into butadiene of claim 1, wherein the energy content of said butadiene enriched product stream supplies such a proportion of the energy required for:
    (a) vaporizing and superheating said hydrocarbonaceous butene rich feed; and
    (b) vaporizing and superheating the water used to supply superheated steam in said reactor feed stream,
    that less than 0.3 kg of natural gas is consumed in steps (a) and (b) for each kg of butadiene produced.

8. The improved low emissions method of converting a hydrocarbonaceous butene rich feed into butadiene of claim 1, wherein the energy content of said butadiene enriched product stream supplies such a proportion of the energy required for:
(a) vaporizing and superheating said hydrocarbonaceous butene rich feed; and
(b) vaporizing and superheating the water used to supply superheated steam in said reactor feed stream,
that less than 0.25 kg of natural gas is consumed in steps (a) and (b) for each kg of butadiene produced.

9. An improved low emissions method of manufacturing butadiene by oxidative dehydrogenation of a hydrocarbonaceous butene rich feed, wherein the improvement comprises the steps of:
vaporizing said hydrocarbonaceous butene rich feed, mixing the vaporized hydrocarbonaceous butene rich feed with superheated steam and an oxygen rich gas to form a reactor feed stream, superheating said reactor feed stream to a temperature of at least 345° C. (650° F.);
oxidatively dehydrogenating said reactor feed stream over a ferritic oxide catalyst, thereby forming a butadiene enriched product stream, wherein the temperature of the butadiene enriched product stream is at least about 510° C. (950° F.);
passing the butadiene enriched product stream at a temperature of at least about 510° C. (950° F.) first through a reactor feed superheater in which the reactor feed stream is superheated by indirect heat exchange with said butadiene enriched product stream to at least 345° C. (650° F.);
passing the butadiene enriched product stream exiting said reactor feed superheater through a steam generator in which water is vaporized by indirect heat exchange with said butadiene enriched product stream exiting said reactor feed superheater to provide vaporized and/or superheated steam;
passing the butadiene enriched product stream exiting said steam generator through a quench tower, a compressor, an aldehyde scrubber, and a C4 absorber, wherein butadiene and C4 compounds are absorbed into an absorption oil,
passing an overhead from said C4 absorber to a thermal oxidizer to generate steam, wherein the steam from the thermal oxidizer is used to supply heat used in the method;
passing the absorption oil to: (i) a degasser tower wherein residual nitrogen, hydrogen, and carbon dioxide are removed from the absorption oil and (ii) a C4 stripper wherein butadiene and the C4 compounds are stripped from the absorption oil and recovered as a crude butadiene product stream,
stripping aqueous liquid from the butadiene enriched product stream to provide an aqueous stream containing dispersed volatile organics,
stripping the dispersed volatile organics from the aqueous stream to produce a resultant aqueous stream, wherein at various stages of the method the resultant aqueous stream is provided to the steam generator;
wherein, during steady operation, any additional heat required to:
vaporize and superheat said hydrocarbonaceous butene rich feed; and
vaporize and superheat the water used to supply superheated steam in said reactor feed stream;
is no more than 130% of the sum of (1) the sensible heat extracted from the butadiene enriched product stream and (2) the heat generated by thermal oxidation of the overhead from the C4 absorber separated from the butadiene enriched product stream.

10. The improved low emissions method of manufacturing butadiene by oxidative dehydrogenation of a hydrocarbonaceous butene rich feed of claim 9, wherein any additional energy required for conversion of said hydrocarbonaceous butene rich feed into said butadiene enriched product stream is no more than 110% of the sum of: (1) the sensible heat extracted from the butadiene enriched product stream and (2) the heat generated by thermal oxidation of the overhead from the C4 absorber separated from the butadiene enriched product stream.

11. In a process for producing butadiene by converting butenes from a butene rich feed stream into butadiene by oxidatively dehydrogenating said butenes in a reaction system which includes a superheater for superheating feed and one or more steam generators for vaporizing water, the improvement comprising:
(a) reacting said butene rich feed stream in an oxidative dehydrogenation reactor to form a butadiene enriched product effluent stream which exits said oxidative dehydrogenation reactor;
(b) feeding said butadiene enriched product effluent stream to a feed superheater, wherein the butadiene enriched product effluent stream is provided to the feed superheater at a temperature of 425° C. (800° F.) or more, oxidative dehydrogenation reactor feed also being provided to the feed superheater;
(c) superheating the oxidative dehydrogenation reactor feed in the feed superheater to a temperature of at least 260° C. (500° F.) with indirect heat transfer of sensible heat from the butadiene enriched product effluent stream to the oxidative dehydrogenation reactor feed;
(d) subsequent to step (c), feeding the butadiene enriched product effluent stream exiting the feed superheater to a steam generator, wherein the butadiene enriched product effluent stream entering the steam generator is at a temperature of at least 205° C. (400° F.); and
(e) vaporizing water in the steam generator with indirect heat transfer of sensible heat from the butadiene enriched product effluent stream to the water.

12. The improvement according to claim 11, wherein the butadiene enriched product effluent stream is provided to the feed superheater at a temperature of from 480° C. to 760° C. (900° F. to 1400° F.).

13. The improvement according to claim 11, wherein the butadiene enriched product effluent stream is provided to the steam generator at a temperature of at least 290° C. (550° F.).

14. The improvement according to claim 11, wherein at least 2300 kJ/kg (1000 BTU/LB) butadiene produced is transferred from the butadiene enriched product effluent stream to the oxidative dehydrogenation reactor feed in the feed superheater by indirect heat exchange.

15. The improvement according to claim 11, wherein from 2300 to 5800 kJ/kg (1000 to 2500 BTU/LB) butadiene produced is transferred from the butadiene enriched product effluent stream to the oxidative dehydrogenation reactor feed in the feed superheater by indirect heat exchange and from 2300 to 7000 kJ/kg (1000 to 3000 BTU/LB) butadiene produced is transferred from the butadiene enriched product effluent stream to the water in the steam generator by indirect heat exchange.

* * * * *